(12) United States Patent
Airaudi et al.

(10) Patent No.: US 6,743,164 B2
(45) Date of Patent: Jun. 1, 2004

(54) ELECTRONIC DEVICE TO DETECT AND GENERATE MUSIC FROM BIOLOGICAL MICROVARIATIONS IN A LIVING ORGANISM

(75) Inventors: Oberto Airaudi, Cuceglio (IT); Roger Rognas, Pompano Beach, FL (US); Lee Weinstein, Arlington, MA (US)

(73) Assignee: Music of the Plants, LLP, Hallandale, FL (US)

( * ) Notice: Subject to any disclaimer, the term of this patent is extended or adjusted under 35 U.S.C. 154(b) by 73 days.

(21) Appl. No.: 10/282,548

(22) Filed: Oct. 29, 2002

(65) Prior Publication Data

US 2003/0106260 A1 Jun. 12, 2003

Related U.S. Application Data

(63) Continuation-in-part of application No. 09/849,756, filed on May 4, 2001, now Pat. No. 6,487,817, which is a continuation-in-part of application No. 09/324,402, filed on Jun. 2, 1999, now abandoned.

(51) Int. Cl.[7] .......................... A61M 21/00; A01G 7/04
(52) U.S. Cl. .......................... 600/27; 47/58.1 R; 47/1.3; 84/600
(58) Field of Search .................. 600/27–28, 544–546; 128/905, 897; 47/58.1 R, 1.3; 84/600

(56) References Cited

U.S. PATENT DOCUMENTS 3,852,914 A    12/1974   Levengood .................. 47/1.3
4,305,402 A    12/1981   Katims ....................... 600/554
4,758,318 A    7/1988    Yoshida ....................... 47/1.3
5,343,871 A    9/1994    Bittman et al. ............. 600/545
5,465,729 A    11/1995   Bittman et al. ............. 600/545
5,540,235 A    7/1996    Wilson .................... 600/545 X
5,775,332 A    7/1998    Goldman ..................... 600/587
5,814,078 A    9/1998    Zhou et al. .................... 607/1
5,974,262 A    10/1999   Fuller et al. ............. 600/545 X
6,067,468 A    5/2000    Korenman et al. ......... 600/547
6,487,817 B2 * 12/2002   Airaudi .................. 47/58.1 R

FOREIGN PATENT DOCUMENTS

| EP | 0459540 A1 | 12/1991 |
| EP | 0848058 A1 | 6/1998 |
| FR | 2638936 A1 | 5/1990 |
| FR | 2676930 A1 | 12/1992 |
| GB | 2210765 A | 6/1989 |
| JP | 09070205 A | 3/1997 |
| JP | 10191793 A | 7/1998 |

* cited by examiner

*Primary Examiner*—John P. Lacyk
(74) *Attorney, Agent, or Firm*—Welsh & Katz, Ltd.

(57) ABSTRACT

A method and apparatus are provided for using microvariations of a biological living organism to generate a sequence of environmental changes perceptible through one of the human senses. The method includes the steps of transforming microvariations within a living organism into an analog electrical signal and generating the sequence of environmental changes perceptible through the human senses based on said analog signal. The sequence of changes can include the generation of music based on the signal, or the control of lighting, aromas, or air movement in the environment of the organism. One example application is the generation of music from electrical microvariations detected in a house plant.

59 Claims, 5 Drawing Sheets

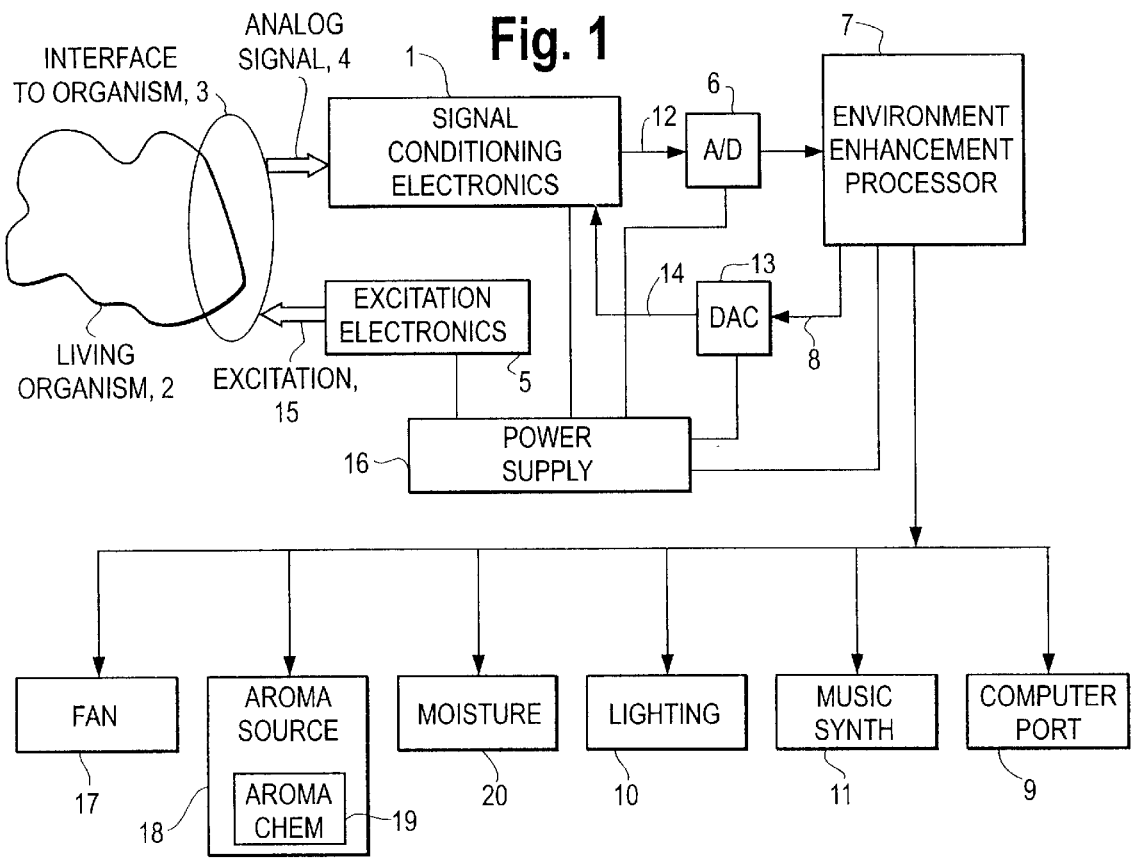
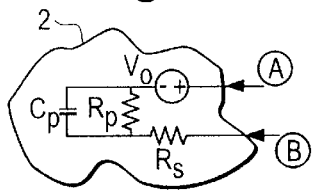
Fig. 2
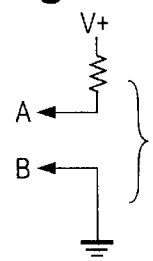
Fig. 2a
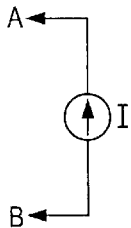
Fig. 2b
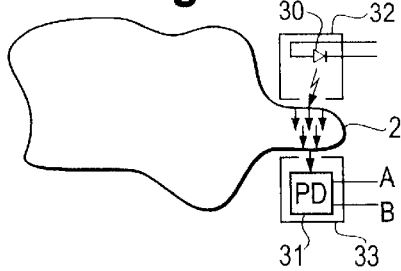
Fig. 3
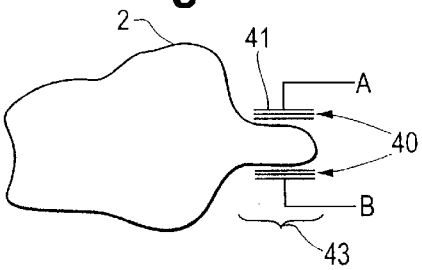
Fig. 4

ELECTRONIC DEVICE TO DETECT AND GENERATE MUSIC FROM BIOLOGICAL MICROVARIATIONS IN A LIVING ORGANISM

FIELD OF THE INVENTION

The field of the invention relates to living organisms and more particularly to the detection of microvariations within living organisms.

BACKGROUND OF THE INVENTION

This application is a continuation-in-part of U.S. patent application Ser. No. 09/849,756, filed on May 4, 2001 now 6,487,817 which is a continuation-in-part of U.S. patent application Ser. No. 09/324,402, filed on Jun. 2, 1999 (abandoned).

In the medical arts there are systems for detection of biologic variations, such as electrocardiographs (ECGs), electroencephalographs (EEGs), lie detectors, etc. There are also other systems to detect biological and bioclimatic variations used for the automatic control of greenhouses and servocontrols which, for that purpose, use sensors which assess environmental conditions, such as humidity and soil moisture content. This invention is different from all of the above because it uses a living organism itself as the signal source of the sensor and the user of the signal it produces.

SUMMARY

A method and apparatus are provided for using microvariations of a biological living organism (such as a plant) to generate pleasing environmental conditions perceptible through one of the human senses, such as by generating music, controlling mood lighting, etc. One embodiment of the present invention includes the steps of detecting microvariations within a living organism, and using data from those microvariations as input to a microprocessor-based musical code generator which plays music through a MIDI music synthesizer.

BRIEF DESCRIPTION OF THE DRAWINGS

FIG. 1 depicts a block diagram of a system for controlling the environment of a living organism in accordance with an illustrated embodiment of the invention;

FIG. 2 depicts a direct-contact example of the Interface block in FIG. 1, including a first-order electrical model of an organism;

FIG. 2a depicts a resistive divider excitation source for use in exciting the direct-contact interface shown in FIG. 2;

FIG. 2b depicts a current source excitation for use in exciting the direct-contact interface shown in FIG. 2;

FIG. 3 depicts an optical embodiment of organism interface 3 in FIG. 2, where light is shined through a portion of a living organism, and microvariations in opacity are measured;

FIG. 4 depicts a capacitive embodiment of organism interface 3 in FIG. 2, where an electric field is applied to a portion of a living organism, and microvariations in the dielectric constant of that portion of the organism are measured;

DETAILED DESCRIPTIONS OF SOME PREFERRED EMBODIMENTS

Figure 5A:
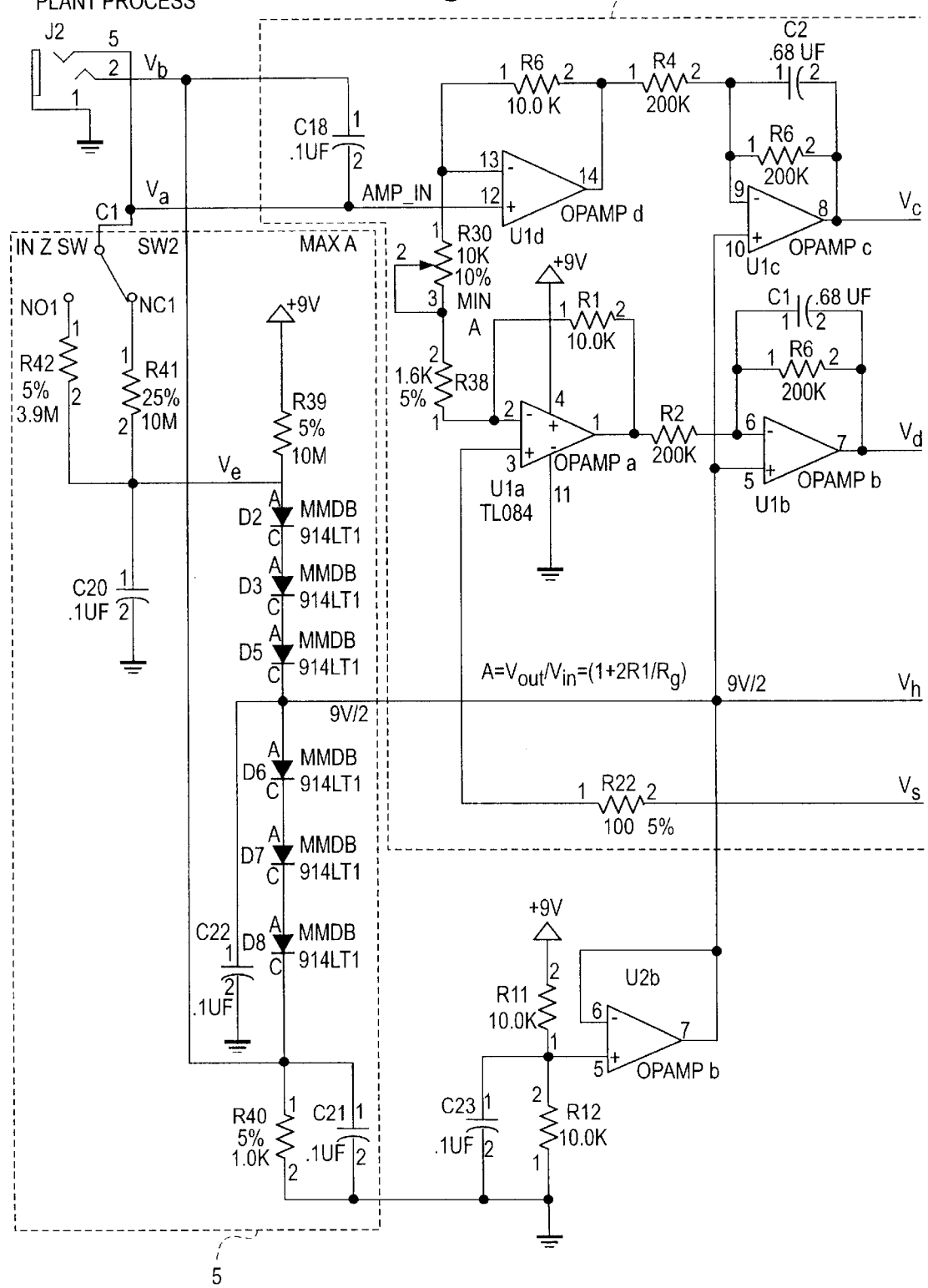
FIGS. 5a and 5b together comprise the analog circuitry portion of a detailed schematic of a preferred embodiment of the present invention.

Disclosed herein are methods and apparatus that may be used to detect microvariations in a biologic living organism, and generate a sequence of changes perceptible through the human senses (e.g., sight, sound, temperature, humidity, etc.) in the environment surrounding that organism or a human participant based on those microvariations. As used herein, the term "biologic living organism" means a plant or a non-human animal. The term "microvariations", as used in this document, shall be construed to include any measurable minute variation within a living organism. Such microvariations can be in electrical impedance, dielectric constant, chemical concentrations, electrochemical potential, electrochemical current, mechanical tension, force, pressure, optical transmisivity, optical reflectivity, reflected or transmitted chromatic value, magnetic or electrical permeability, etc. The term "microvariations" does not mean bio-frequency spectrum signals emanating from the living organism.

One embodiment of the disclosed invention has been found effective in detecting microvariations in a living organism and generating pleasing melodies based on these microvariations. Living organisms, including plants, are believed capable of varying their internal bio-chemical and bio-electric state as a consequence of external situations. Plants are, therefore, capable of some sort of rudimentary "feelings".

FIG. 1 shows a block diagram of the apparatus of the present invention. Signal conditioning electronics 1 connects to living organism 2 through interface 3. Microvariations within organism 2 produce analog signal 4 which feeds signal conditioning electronics 1. In some preferred embodiments, excitation electronics 5 applies an excitation signal 15 to organism 2, and microvariations in the response of organism 2 to excitation signal 15 are measured through analog signal 4. In preferred embodiments utilizing purely passive measurement (such as measurement of microvariations in electrochemical offset voltage Vo produced by organism 1), no excitation signal is needed and thus excitation electronics 5 are not employed.

In a preferred embodiment, conditioning electronics 1 provides amplification, level shifting, and filtering to best utilize the dynamic range of Analog to Digital Converter (ADC) 6 for measurements of microvariations in signal 4. ADC 6 feeds digital processing electronics 7. In a preferred embodiment, digital processing electronics 7 uses data received from ADC 6 to control timing and melodic progression of a sequence of digital musical note codes generated. The digital musical note codes generated in processor 7 are fed to MIDI music synthesizer 9.

In another preferred embodiment, digital processor 7 uses data received from ADC 6 to control timing and progression of lighting control codes sent to lighting controller 10, which may be used, for instance, to provide pleasing and continually changing mood lighting in a room, or to alter growth enhancing lighting on plants, etc.

In another preferred embodiment, digital processor 7 uses data received from ADC 6 to control a sequence of releases of moisture into the environment of organism 2, by moisture releaser 20, which may be, for example, a humidifier or an atomizer or sprayer.

In another preferred embodiment, digital processor 7 uses data received from ADC 6 to control a sequence of releases of aromatic chemicals 19 into the environment of organism 2. The aroma source 18, which may, for instance, be a controllable evaporator.

In another preferred embodiment, digital processor 7 uses data received from ADC 6 to control air movement over time in the environment of organism 2, by controlling the speed and/or direction of fan 17.

In a preferred embodiment, lighting and/or music codes may be fed from processor 7 to computer port 11, and a personal computer may be connected to computer port 11 and used as a music synthesizer or lighting controller. The term "music" as used in this document, shall be construed to include sound effects such as rain sounds, seashore sounds, wind sounds, voice sounds etc., which are commonly synthesizable, or recorded and reproduced. Data fed to port 11 could, for instance, be used to choose which tracks were to be played from one or more compact disks, and/or in what order and/or at what volume those tracks were to be played.

To facilitate using a less expensive, lower resolution ADC, Digital to Analog Converter (DAC) 13 may be controlled by processor 7 to provide level shifting signal 14 to signal conditioning electronics 1 to effectively dynamically level-shift the signal 12 being fed to ADC 6. This effectively expands the dynamic range of ADC 6 to any value needed, and the resolution of the overall delta-sigma ADC implemented through this topology may be chosen by setting the overall signal gain of signal conditioning electronics 1. Rapid double sampling before and after adjustments of DAC 13 allows differential nonlinearity of the effective overall delta-sigma ADC to remain almost as good as differential nonlinearity of ADC 6. Integral nonlinearity may be worse in this topology than if a higher resolution ADC 6 were employed, but since the application for the present invention is to measure short-term microvariations, integral nonlinearity of ADC 6 is not a primary concern.

Power supply 16 provides the various power supply voltages used by excitation electronics 5, signal conditioning electronics 1, ADC 6, processor 7, DAC 13, and may also provide power for environment enhancing electronics (such as lighting control 10, music synthesizer 9, etc.).

In many embodiments, the level shifting provided by taking processor-controlled feedback through DAC 13 to signal conditioning electronics 1 may equivalently be accomplished by taking processor-controlled feedback through DAC 13 to excitation electronics 5. DAC 13 may be implemented in a variety of ways depending on cost considerations and the desirability of serial or parallel interface to processor 7. Possible DAC implementations include but are not limited to: R-2R ladder, frequency to voltage (F to V) converter, charge pump, timed gated integrator, etc. Since many embodiments of the present invention are intended only to measure short-term microvariations, the DAC topology used may be either absolute or differential in nature, and long-term drift and integral nonlinearity of the DAC may be of little concern, allowing less expensive DAC implementations.

FIGS. 2, 3, and 4 depict different preferred embodiments for measurement interface 3 in FIG. 1. FIG. 2 depicts a measurement interface comprising two direct electrical contacts A and B to the organism 2 under observation. A first order electrical model for the organism under observation is comprised of parallel capacitance Cp, parallel resistance Rp, series resistance Rs, and series voltage source Vo. Microvariations in resistances Rp and Rs may be representative of changes in bulk and surface conductivity of the organism. Microvariations in voltage Vo may be representative of differential surface chemistry between the contacts at points A and B. Microvariations in capacitance Cp may be representative of chemical balance changes within the organism.

FIGS. 2a and 2b depict two preferred embodiments for implementing the excitation electronics 5 for an embodiment of the present invention utilizing a direct-contact organism interface as shown in FIG. 2, where the intent is to measure microvariations in electrical resistance of the organism (modeled by Rp and Rs in FIG. 2). FIG. 2a provides an excitation current through the organism by making the organism into a part of a resistive voltage divider (such as one side of a Wheetstone bridge). In FIG. 2b, a current source is used as an excitation for the organism. For the excitation circuits in FIGS. 2a and 2b, microvariations in electrical resistance of organism 2 cause microvariations in the voltage sensed between contacts A and B. Excitation voltage source V+ and excitation current source I may be either DC or AC sources. In one preferred embodiment, an AC excitation source is used to avoid plating contact metals from contacts A and B onto organism 2 over the long term, and Signal Conditioning electronics include AC to DC conversion circuitry so that a conventional DC ADC may be used.

FIG. 3 and FIG. 4 depict preferred embodiments of organism interface 3 which make no direct electrical connection to the organism under observation. In FIG. 3, photo source module 32 contains light-emitting diode (LED) 30, which emits light in response to electrical excitation by excitation electronics 5. Light from the LED passes through a portion of organism 2 and photo detector 31 contained within light sensing module 33 produces an electrical signal on terminals A and B related to the amount of light passing through organism 2 from LED 30. Microvariations in opacity of organism 2 caused by chemical composition changes, etc. produce microvariations in the signal detected between points A and B. Depending on the component used to implement photo detector 31 (such as photodiode, cadmium sulphide photo-resistor, etc., an excitation signal from excitation electronics 5 may be needed for the photo detector as well as the photo source module. In an alternate embodiment, photo detector 31 could be configured to detect light reflected off organism 2 from LED 30, rather than light transmitted through organism 2 by LED 30. In either reflected or transmitted embodiments, a color filter may be used over light source or photo detector, allowing sensitivity to microvariations in reflected or transmitted light of a particular spectral content. Similarly, multiple color filters can be used with multiple photodetectors, to detect microvariations in reflected or transmitted spectral distribution of light.

FIG. 4 depicts an embodiment of organism interface 3 in FIG. 2 for measuring microvariations in the dielectric constant of an organism. Conductive plates 41 and 42 form a capacitor 43, with plate insulators 40 and organism 2 comprising the dielectric of the capacitor. Since the capacitance of a capacitor is a function of the dielectric constant of the dielectric between its plates, the capacitance of capacitor 43 is a function of the dielectric constant of organism 2. For this embodiment of organism interface 3, excitation electronics 5 may comprise an oscillator circuit, such that the frequency of oscillation is a function of the capacitance of capacitor 43. In such an embodiment, ADC 6 may comprise a frequency counter.

Figure 5B:
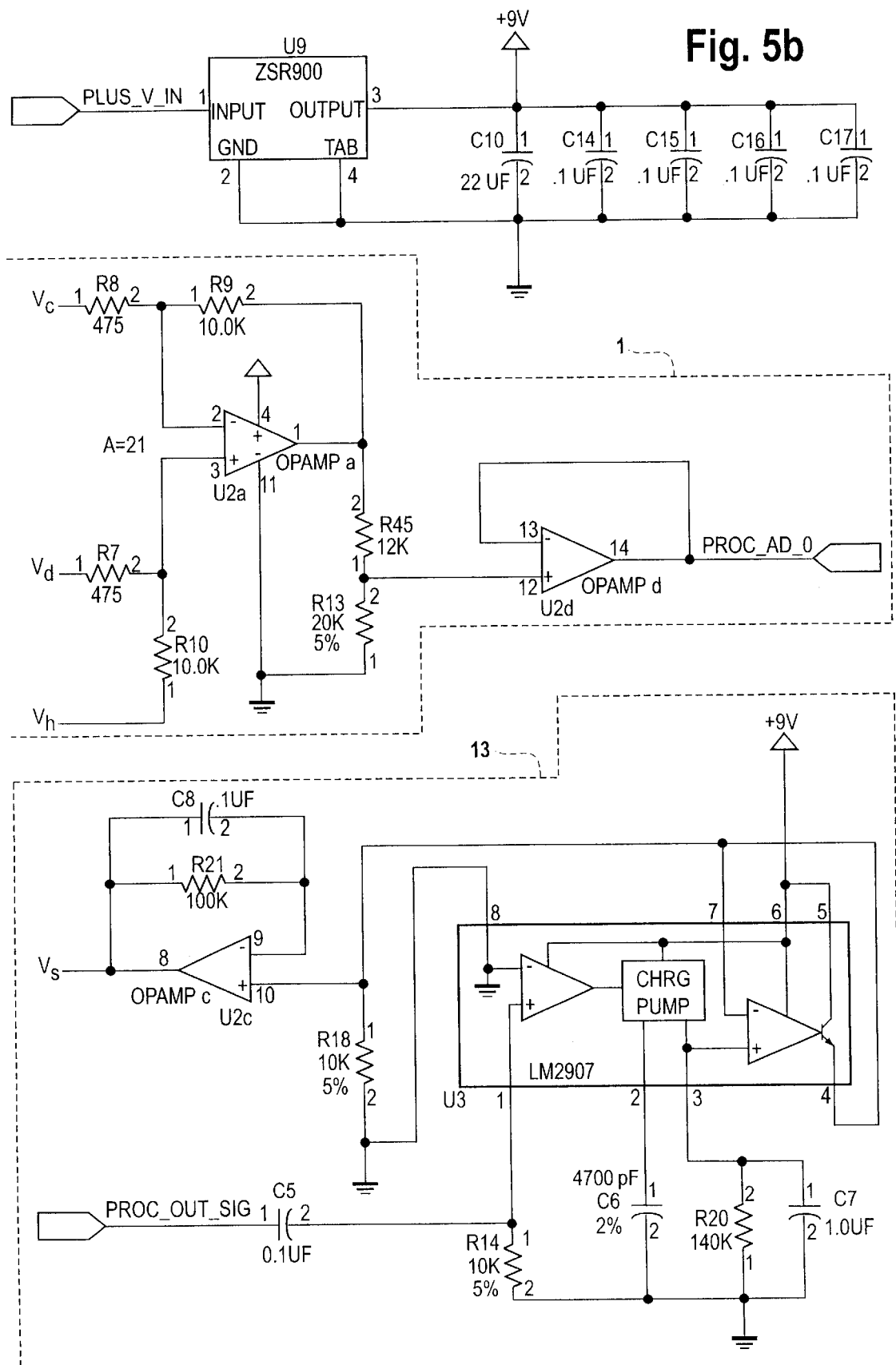
Figure 5C:
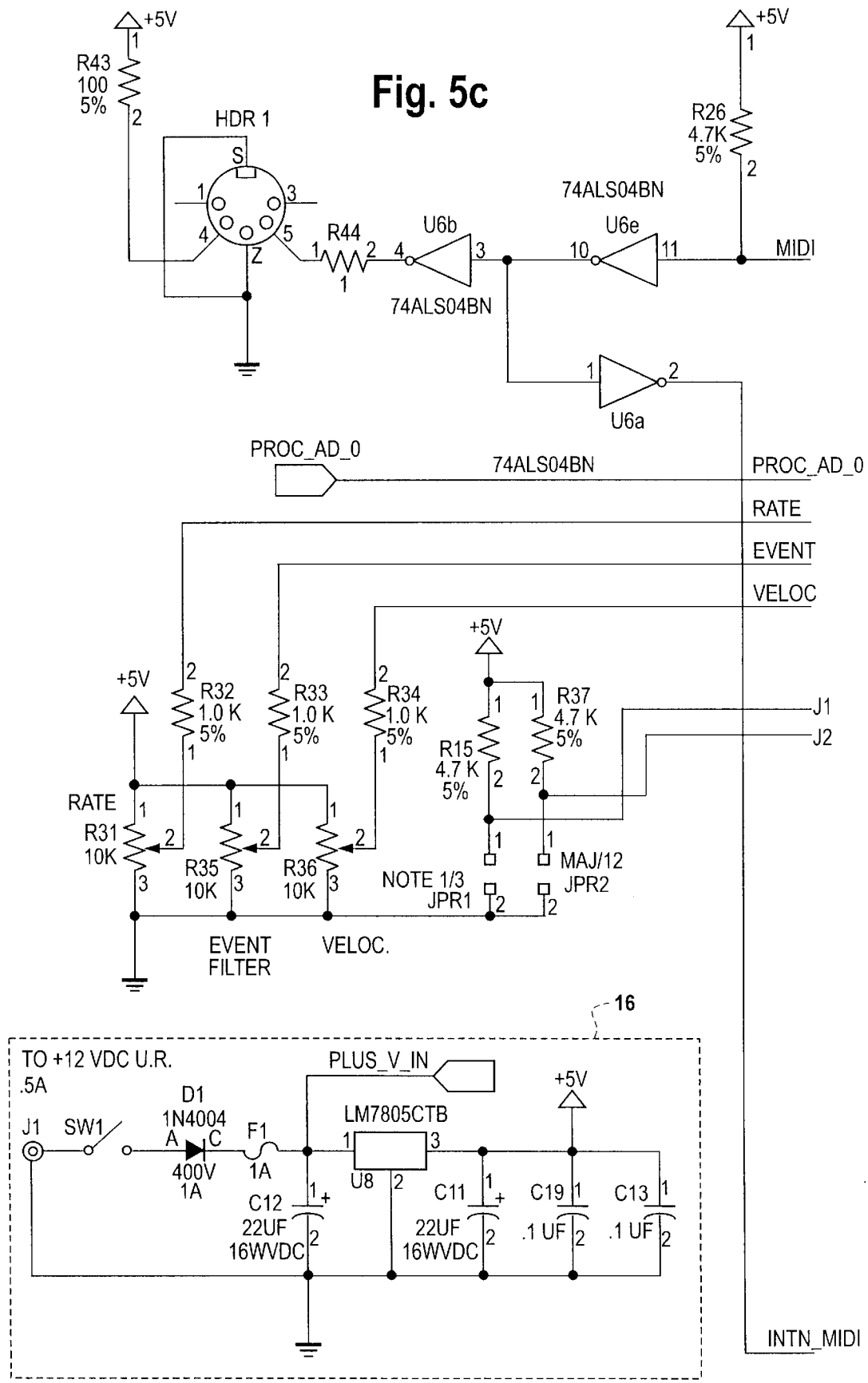
FIGS. 5c and 5d together comprise a detailed schematic diagram of the digital circuitry portion of a preferred embodiment of the present invention; and APPENDIX I provides object code that may be used by the microcontroller of FIG. 5d.
Figure 5D:
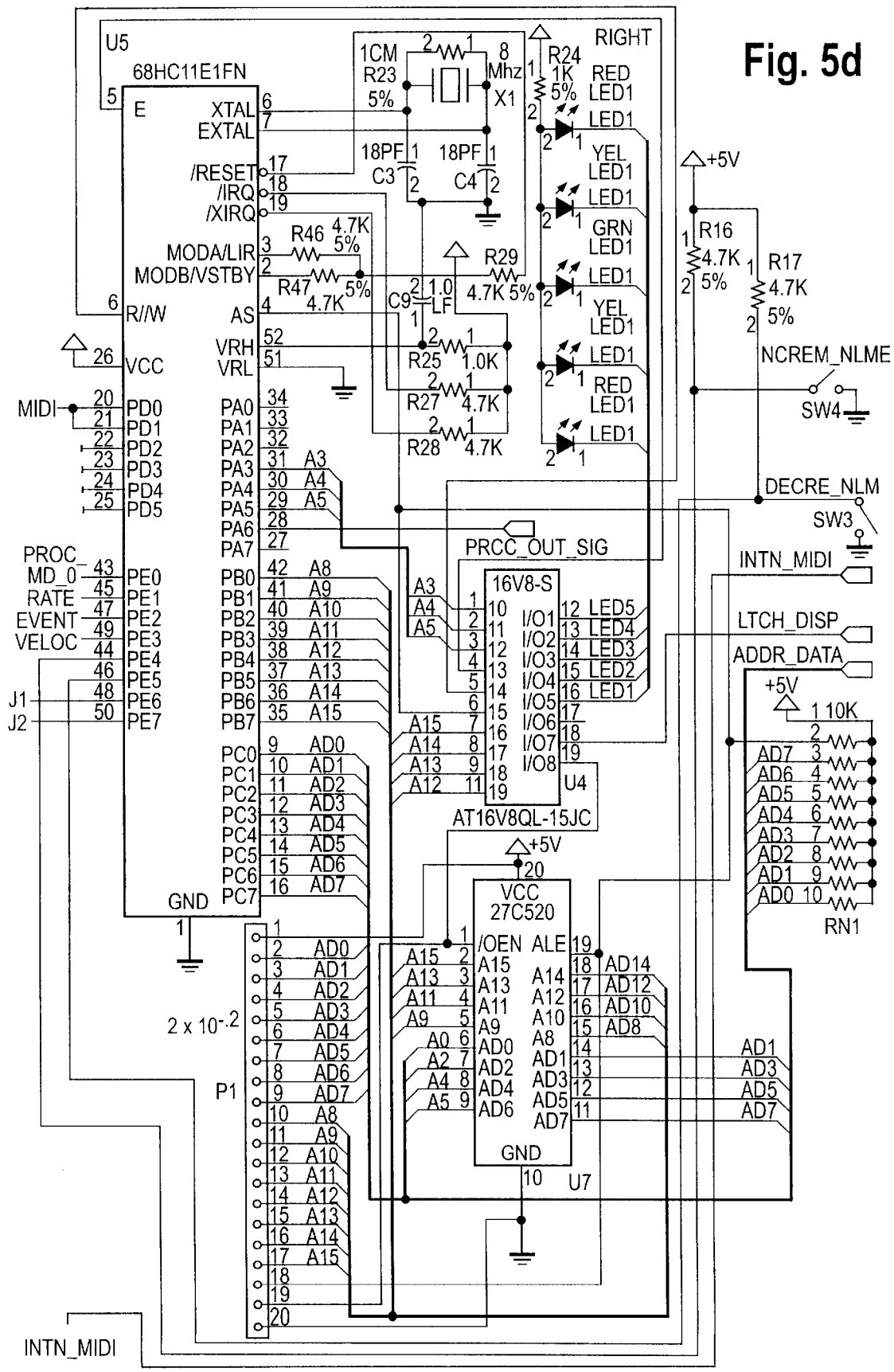

A detailed schematic diagram of a preferred embodiment of the present invention is shown in FIGS. 5a, 5b, 5c, and 5d. FIGS. 5a and 5b together comprise the analog electronics of blocks 1 (signal processing electronics), 5 (excitation electronics), 13 (DAC), and 6 (ADC) of FIG. 1, as well as part of block 16 (power supply) of FIG. 1. FIGS. 5c and 5d comprise the digital circuitry of processor block 7 of FIG. 1, as well as the remainder of power supply block 16 of FIG. 1.

Dotted line 5 of FIG. 5a surrounds circuitry used to implement excitation circuitry block 5 in FIG. 1. The series combination of R39, D2, D3, D5 is connected between the 9V power supply rail and the Vh power supply rail. Current flowing through this series combination creates a voltage Ve approximately (1.8V above Vh) across capacitor C20. The series combination of R40, D6, D7, and D8 is connected between the Vh power supply rail and ground. Current flowing through this series combination creates a voltage Vb approximately (1.8V below Vh) across capacitor C21. The differential voltage between Ve1 and Ve2 is applied to the series combination of the organism under observation, and resistor R41 or R42 (depending on the position of range switch SW2), in a manner analogous to the resistive divider excitation circuit shown in FIG. 2a. Defining Vb and Ve as 3 diode voltage drops away from Vh guarantees that the ground referenced input voltages Va and Vb from the organism under observation are always within the linear range of the op amps used in the signal conditioning circuitry. The differential excitation voltage between Va and Vb is connected to the organism under observation through probe jack J2.

Dotted line 1 in FIGS. 5a and 5b surrounds circuitry used to implement signal conditioning circuitry block 1 in FIG. 1. Op amps U1a, U1b, U1c, and U1d (along with associated resistors R3, R4, R6, R38, R30, R1, R2, and R5) serve as a differential amplifier which serves to amplify the difference between level shifter feedback voltage Vs and voltage Va sensed from the organism under observation. Capacitors C1 and C2 serve to symmetrically provide pole-zero low-pass function to the gain path to limit responsiveness of the system to electromagnetic interference. Capacitor C18 adds another pole to the transfer function, creating a second-order low-pass circuit, to further limit susceptibility to electromagnetic interference.

Op amps U2a and U2d, in conjunction with resistors R8, R9, R7, and R10 serve as a differential-to-single-ended subtractor amplifier, amplifying the difference voltage between Vc and Vd by a factor of R9/R8 and producing a single-ended output voltage which is referenced to ground. The combination of R45, R13, and op amp U2d attenuates this voltage by a factor of R13/(R13+R45), and unity-gain buffers this voltage to provide input signal PROC_AD_0 for the ADC. Power supply circuitry in FIG. 5a comprising U9, C10, C14, C15, C16, and C17 is powered by power supply signal PLUS_V_IN from power supply circuitry in FIG. 5c, and provides 9V regulated power for all circuitry in FIGS. 5a and 5b. Op amp U2b, in conjunction with R11, R12, and C23 provides a derived additional 4.5V power supply rail around which the afore mentioned excitation voltages Ve1 and Vb are defined.

Dotted line 13 in FIG. 5b surrounds circuitry used to implement DAC block 13 in FIG. 1. The DAC function in FIG. 5b may be implemented as a frequency to voltage converter (FVC). The FVC comprises U3, and associated discrete components C4, R14, C6, R20, C7, and R18. The output of the FVC is buffered through a unity-gain buffer comprising U2c, R21, and C8. Microprocessor U5 in FIG. 5d controls the FVC through digital signal PROC_OUT_SIG, which is AC coupled into the FVC through capacitor C5. During normal operation, the voltage Va sensed from the organism under observation has long-term large drift superimposed on top of the measured microvariations. To keep the voltage PROC_AD_0 within the range of the microprocessor's internal ADC, the processor occasionally adjusts the frequency fed to the FVC, causing the output voltage of the FVC to adjust, which level-shifts the signal PROC_AD_0.

All of the electronics in FIGS. 5c and 5d (with the exception of the circuitry surrounded by dotted line 16) comprises processor block 7 in FIG. 1. Additionally, microprocessor U5 contains an internal ADC, which comprises ADC block 6 of FIG. 1.

Potentiometer R31, R35, and R36 provide analog voltages to three multiplexed inputs of the ADC that is internal to microprocessor U5. Microprocessor U5 periodically reads the positions of potentiometers R31, R35, and R36, and the setting of these potentiometers are used to set parameters of how variations in signal PROC_AD_0 (analogous to microvariations in organism 2) are processed. Potentiometer R31 allows adjustment or the rate at which microprocessor U5 samples and processes microvariations in signal PROC_AD_0. Potentiometer R35 adjusts how large a microvariation it takes to meet certain processing thresholds. Potentiometer R36 adjusts the MIDI velocity of MIDI note codes generated by microprocessor U5. Adjustment of MIDI velocity is analogous, for instance, to adjusting how hard a piano key is stuck when playing a piano.

Jumpers JPR1 in FIG. 5c provides an input to microprocessor U5 which chooses between microprocessor U5 generating one note at a time in response to microvariations in organism 2, or generating triads of notes in response to microvariations in organism 2. Jumper JPR2 provides an input to microprocessor U5 that chooses between music being generated according to a major scale, or according to a 12-note scale.

Microprocessor U5 controls LED1, LED2, LED3, LED4, and LED5 to provide a visual indication of where within the range of the ADC the signal PROC_AD_0 is. If either the red LED5 or the red LED1 are lit, that indicates that the ADC is at an extreme end of its range, indicating that the level-shifting frequency-to-voltage converter DAC is unable to bring the signal back in range. Such a condition indicates a likely misconnection or misconfiguration of the interface to organism 2.

The microvariations sensed through the present invention may have various possibilities of linking. For instance, a voltage controlled audio frequency generator, or a MIDI interface audio generator, or a computerized interface portal, or a non-computerized one, or the management of systems of light mixing or electrical devices such as valves, pumps or electric engines or other servocontrols.

Such devices can have multiple uses, such as, for example, light and sound shows, play and entertainment, reproduction of artistic sound compositions through audiovisual supports, direct control of greenhouses, light sources, home and industrial uses, or it can allow the study of all phenomena linked to he sensitivity of the living biological organisms connected to the device.

Microprocessor U5 outputs a MIDI output (i.e., a serial output at 31,200 baud) that is representative of the change. An attached MIDI device translates these signals into musical tones.

In order to generate musical tones, the microprocessor periodically converts the analog output PROC_AD_0 into a digital value through its internal ADC. The microprocessor then monitors the converted digital value to determine when that digital value has changed. For example, when the monitored digital value increases, the microprocessor may send a serial MIDI command string to activate a musical note via the UART of the microprocessor. Similarly, if the monitored value decreases, the microprocessor may turn off the note. If the monitored digital value is close to an upper or lower limit of the ADC range, then the microprocessor may change the frequency driving the frequency to voltage converter to bring the input of the ADC closer to a center of its operating range.

Within the microprocessor U5, the sequence of samples from the ADC is converted to a sequence of musical note codes. Connector HDR1 is provided to connect the note code output from the microprocessor to a MIDI music synthesizer.

A number of switch inputs may be provided to enhance music quality. In FIG. 5d, switches SW3 and SW4 are used to increment and decrement musical instrument designation codes that the microprocessor sends to the MIDI synthesizer.

Turning now to the software, Appendix I shows a number of software modules that interact to provide the functionality discussed above. For example, an INITIALIZATION ROUTINE is shown on page 2. The INITIALIZATION ROUTINE functions to set up the system variables, registers, the interrupt vector, etc. to allow the system to operate properly.

Pages 2–3 show the MAIN program. The MAIN program functions as the main program loop for calling the appropriate subroutines. The MAIN program functions to provide the timing of the generation of the individual musical notes (e.g., input signal sampling frequency, MIDI note code generation, etc.). The MAIN program reads the Rate knob position as an input.

One subroutine called by the MAIN program is the AUTORANGE loop (AU_RG) shown on page 3 of Appendix I. The AUTORANGE loop is a software signal follower that may be used to regulate the device internal parameters to follow the signal from the plant (i.e., the AUTORANGE loop may be used to generate the feedback signal). In effect, the AUTORANGE loop functions to center a measurement window around the difference signal. If the DC level of the difference signal should rise or fall, the AUTORANGE loop may detect and compensate for the change. The effect is that the AUTORANGE loop functions to maintain the dynamic range of the system 10 by maintaining an average signal value within the center of the window.

The MAIN program also calls the CONVERSION ROUTINE on page 4 of Appendix I. The CONVERSION ROUTINE functions to convert the knob position of the Rate and Event Filter control knobs. The outputs of the CONVERSION ROUTINE are the variables "RATE" and "INT".

The MAIN program also calls the ELAB routine on page 5 of Appendix I. The ELAB routine functions to provide input data acquisition, computing, event filtering and 1 or 3 notes code generation. The 1 or 3 notes code generation refers to the ability of the system to provide one note at a time or three notes at a time using a running status message.

The ELAB routine converts the input signal from the plant to a form (a chromatic scale) usable by the other routines. It also reduces the input range to ⅓ based upon the position of the ⅓ switch position.

If the 12/M switch is set, the ELAB routine transforms the chromatic scale from a dodecaphonic scale to a major scale (i.e., by calling the SCALA routine) or visa versa. The ELAB routine may then generate the MIDI musical note code to be sent to the MIDI output via a serial communication interface (3 notes at a time or 1 note at a time based upon the ⅓ switch position). The ELAB routine may then call the MIDI code assembler routines (NOTE_ON and NOTE_OFF).

The ELAB routine receives as inputs the difference signal (ADRI register), SW (switch position image variable), INT (event filter knob position), NTON, NTOFF, NT1 and NT2. Outputs of the ELAB routine may be a temporary variable (TEMP) and variables that allow for the control of note code generation (NTON, NTOFF, NT1, NTW).

The SCALA routine of page 5 of Appendix I is called by the ELAB routine. The SCALA routine computes musical notes (e.g., from a chromatic 12 note octave scale to a 7 note octave major scale). The SCALA routine may perform the scaling based upon codes retrieved from a code table labeled "TABLE".

The SCALA routine may receive as an input the temporary value (TEMP). The SCALA routine outputs a new note code in the internal register A (the A accumulator).

The routines NOTE_ON, NOTE_OFF and ANOFF are string code assemblers. The NOTE_ON routine calls the TX routine to send the note to be played to MIDI out. The NOTE_OFF routine calls the TX routine to transmit a code to terminate a note. The ANOFF routine calls the TX routine to send an "all notes off" code to the MIDI out.

The Tex. routine is a serial communication device transmission routine called by the string code assemblers. It retrieves MIDI codes from the A accumulator and delivers the codes to the MIDI output.

The FTOV is an internal interrupt service routine. It loads into an internal timer register the content of the variable MSB from AU_RG and periodically generates an interrupt to control the frequency to voltage converter.

The foregoing detailed description has been given for clearness of understanding only, and no unnecessary limitation should be understood therefrom, as modifications will be obvious to those skilled in the art.

MVAU_002.LST

M68HC11 Absolute Assembler   Version 2.70C:mvau_tx.ASC

```
 1 A                     *****************************
 2 A                     * MV PRG   REL_1  05/25/02 *
 3 A                     *****************************
 4 A
 5 A
 6 A
 7 A                     ************* EQUATES *************
 8 A
 9 A      05C0    HDLY      EQU    $05C0
10 A      0040    BIT6      EQU    $40
11 A      0080    BIT7      EQU    $80
12 A      0018    TOC2      EQU    $18
13 A      0020    TCTL1     EQU    $20
14 A      0023    TFLG1     EQU    $23
15 A      0000    LEDS      EQU    $00           ;PORT A
16 A      000A    PORTE     EQU    $0A
17 A      0022    TMSK1     EQU    $22
18 A      0003    IPORTC    EQU    $03           ;SISTEMARE
19 A      1003    PORTC     EQU    $1003
20 A      0009    DDRD      EQU    $09
21 A      0008    PORTD     EQU    $08
22 A      0028    SPCR      EQU    $28
23 A      002C    SCCR1     EQU    $2C
24 A      002D    SCCR2     EQU    $2D
25 A      002E    SCSR      EQU    $2E
26 A      002B    BAUD      EQU    $2B
27 A      0039    OPTION    EQU    $39
28 A      0030    ADCTL     EQU    $30
29 A      0031    ADR1      EQU    $31
30 A      0032    ADR2      EQU    $32
31 A      0033    ADR3      EQU    $33
32 A      0034    ADR4      EQU    $34
33 A      002F    SCDR      EQU    $2F
34 A      0026    PACTL     EQU    $26
35 A 0000
36 A      0008    __V__     EQU    %00001000
37 A      0010    _G___     EQU    %00010000
38 A      0018    R____     EQU    %00011000
39 A      0020    RG__R     EQU    %00100000
40 A      0028    __G_      EQU    %00101000
41 A      0030    ____R     EQU    %00110000
42 A      0038    R__GR     EQU    %00111000
43 A 0000
44 A                     ************* VARIABLES *************
45 A
46 A      0000              ORG    $00
47 A
48 P 0000 0001    NTON      RMB    1             ;NOTE ON VALUE
49 P 0001 0001    NTOFF     RMB    1             ;NOTE OFF VALUE
50 P 0002 0001    NT1       RMB    1             ;NOTE 1 QUEUE
51 P 0003 0001    NT2       RMB    1             ;NOTE 2 QUEUE
52 P 0004 0001    VEL       RMB    1             ;MIDI VELOCITY
                                                 ;EVENT FILTER AMOUNT
53 P 0005 0001    INT       RMB    1             
                                                 ;AUTORANGE NO OF AMOUNT
54 P 0006 0001    AR        RMB    1             
                                                 CICLES TO SELECT SPEED
55 P 0007 0001    ARFLG     RMB    1             ;AUTORANGE ON FLAG
56 P 0008 0001    SW        RMB    1             ;IMMAGINE SWITCHES
```

Page 1

Appendix I

```
                                      MVAU_002.LST
 57 P 0009 0002       MSB       RMB     2                      ;AUTORANGE DAC MSB
 58 P 000B 0002       RATE      RMB     2                      ;SAMPLING RATE

M68HC11 Absolute Assembler    Version 2.70C:mvau_tx.ASC

59 P 000D 0002       TEMP      RMB     2                      ;TEMPORARY VARIABLE
FOR SCALA ROUTINE
 60 P 000F 0002       ARDEL     RMB     2                      ;AUTORANGE INCREM E
DECREM ROUTINS DELAY
 61 A 0011
 62 A 0011                      ************ INITIALIZATION ROUTINE ************
 63 A
 64 A
 65 A       2000                ORG     $2000
 66 A
 67 A 2000            INIT      LDX     #$1000
 68 A 2000 CE1000               LDS     #$01FF
 69 A 2003 8E01FF               LDAA    #$00
 70 A 2006 8600                 STAA    LEDS,X                 ;PORT A
 71 A 2008 A700                 CLRA
 72 A 200A 4F                   STAA    DDRD,X
 73 A 200B A709                 STAA    SCCR1,X
 74 A 200D A72C                 LDD     #HDLY
 75 A 200F CC05C0                STD     MSB
 76 A 2012 DD09                 LDAA    #BIT6
 77 A 2014 8640                 STAA    TCTL1,X
 78 A 2016 A720                 STAA    TFLG1,X
 79 A 2018 A723                 STAA    TMSK1,X
 80 A 201A A722                 LDAA    #$20
 81 A 201C 8620                 STAA    ARDEL
 82 A 201E 970F                 STAA    ARFLG
 83 A 2020 9707                 LDAA    #$07
 84 A 2022 8607                 STAA    PORTD,X
 85 A 2024 A708                 STAA    SPCR,X
 86 A 2026 A728                 LDAA    #$0C
 87 A 2028 860C                 STAA    SCCR2,X
 88 A 202A A72D                 LDAA    #$10
 89 A 202C 8610                 STAA    SCSR,X
 90 A 202E A72E                 LDAA    #$20                   ;SET BAUD RATE MIDI
 91 A 2030 8620
                                STAA    BAUD,X
 92 A 2032 A72B                 LDAA    #$93                   ;PSU ADC ENABLE
 93 A 2034 8693                 STAA    OPTION,X
 94 A 2036 A739                 LDAA    #$32                   ;SET ADC
 95 A 2038 8632                 STAA    ADCTL,X
 96 A 203A A730                 BSET    PACTL,X,#$08
 97 A 203C 1C2608               LDAA    #$08
 98 A 203F 8608                 STAA    RATE
 99 A 2041 970B                 JSR     ANOFF                  ;ALL NOTES OFF
100 A 2043 BD21E5               CLI
101 A 2046 0E
102 A
103 A                           ************ MAIN ************
104 A
105 A
106 A 2047 18DE0B    MAIN       LDY     RATE
107 A 204A 1809      R1         DEY
108 A 204C 26FC                 BNE     R1
109 A 204E 18DE0B               LDY     RATE
110 A 2051 1809      R2         DEY
111 A 2053 26FC                 BNE     R2
112 A 2055 18DE0B               LDY     RATE
```

Page 2

Appendix I

```
                              MVAU_002.LST
113 A 2058 1809         R3          DEY
114 A 205A 26FC                     BNE       R3
115 A 205C 18DE0B                   LDY       RATE
116 A 205F 1809         R4          DEY
```

M68HC11 Absolute Assembler    Version 2.70C:mvau_tx.ASC

```
117 A 2061 26FC                     BNE       R4
118 A
119 A 2063 A60A                     LDAA      PORTE,X
120 A 2065 84C0                     ANDA      #%11000000
121 A 2067 9108                     CMPA      SW
122 A 2069 2705                     BEQ       M1
123 A 206B 9708                     STAA      SW
124 A
125 A 206D BD21E5                   JSR       ANOFF
126 A 2070 BD2137      M1           JSR       CONV
127 A 2073 BD207C                   JSR       AU_RG
128 A 2076 BD2148                   JSR       ELAB
129 A
130 A 2079 7E2047                   JMP       MAIN
131 A
132 A
133 A                  *************** ROUTINES ***************
134 A
135 A
136 A 207C A631        AU_RG        LDAA      ADR1,X           ;AUTORANGE
137 A 207E 8120                     CMPA      #$20
138 A 2080 231D                     BLS       INCREM
139 A 2082 A631                     LDAA      ADR1,X
140 A 2084 81E0                     CMPA      #$E0
141 A 2086 2263                     BHI       DECREM
142 A 2088 86FF                     LDAA      #$FF
143 A 208A 970F                     STAA      ARDEL
144 A 208C 9607                     LDAA      ARFLG
145 A 208E 2604                     BNE       AU1
146 A 2090 8608                     LDAA      #__V__
147 A 2092 A700                     STAA      LEDS,X
148 A 2094 A631        AU1          LDAA      ADR1,X
149 A 2096 39                       RTS
150 A
151 A 2097 18DE0F      AR_DLY       LDY       ARDEL            ;AUTORANGE DELAY
152 A 209A 1809        ARL          DEY
153 A 209C 26FC                     BNE       ARL
154 A 209E 39                       RTS
155 A
156 A 209F 8628        INCREM       LDAA      #___G_           ;INCREMENT ROUTINE
157 A 20A1 A700                     STAA      LEDS,X
158 A 20A3 9607                     LDAA      ARFLG
159 A 20A5 8110                     CMPA      #$10
160 A 20A7 233E                     BLS       I_RTN
161 A 20A9 8630                     LDAA      #___R
162 A 20AB A700                     STAA      LEDS,X
163 A 20AD 9606        INCR1        LDAA      AR
164 A 20AF 8103                     CMPA      #$03
165 A 20B1 2307                     BLS       INCR2
166 A 20B3 8620                     LDAA      #$20
167 A 20B5 970F                     STAA      ARDEL
168 A 20B7 BD21E5                   JSR       ANOFF
169 A 20BA 18DE09      INCR2        LDY       MSB
170 A 20BD 1808                     INY
171 A 20BF 188C0800                 CPY       #$0800
```

Appendix I

```
                                        MVAU_002.LST
172 A 20C3 2308                 BLS     INCR3
173 A 20C5 18CE05C0             LDY     #$05C0
174 A 20C9 8638                 LDAA    #R__GR
```

M68HC11 Absolute Assembler    version 2.70C:mvau_tx.ASC

```
175 A 20CB A700                 STAA    LEDS,X
176 A 20CD 18DF09       INCR3   STY     MSB
177 A 20D0 BD2097               JSR     AR_DLY
178 A 20D3 A631                 LDAA    ADR1,X
179 A 20D5 8150                 CMPA    #$50
180 A 20D7 7C0006               INC     AR
181 A 20DA 23D1                 BLS     INCR1
182 A 20DC 7F0007               CLR     ARFLG
183 A 20DF 7F0006               CLR     AR
184 A 20E2 86FF                 LDAA    #$FF
185 A 20E4 970F                 STAA    ARDEL
186 A 20E6 39                   RTS
187 A 20E7 7C0007       I_RTN   INC     ARFLG
188 A 20EA 39                   RTS
189 A
190 A 20EB 8610         DECREM  LDAA    #_G___           ;DECREMENT ROUTINE
191 A 20ED A700                 STAA    LEDS,X
192 A 20EF 9607                 LDAA    ARFLG
193 A 20F1 8110                 CMPA    #$10
194 A 20F3 233E                 BLS     D_RTN
195 A 20F5 8618                 LDAA    #R____
196 A 20F7 A700                 STAA    LEDS,X
197 A 20F9 9606         DECR1   LDAA    AR
198 A 20FB 8103                 CMPA    #$03
199 A 20FD 2307                 BLS     DECR2
200 A 20FF 8620                 LDAA    #$20
201 A 2101 970F                 STAA    ARDEL
202 A 2103 BD21E5               JSR     ANOFF
203 A 2106 18DE09       DECR2   LDY     MSB
204 A 2109 1809                 DEY
205 A 210B 188C03C0             CPY     #$03C0
206 A 210F 2208                 BHI     DECR3
207 A 2111 18CE05C0             LDY     #$05C0
208 A 2115 8620                 LDAA    #RG__R
209 A 2117 A700                 STAA    LEDS,X
210 A 2119 18DF09       DECR3   STY     MSB
211 A 211C BD2097               JSR     AR_DLY
212 A 211F A631                 LDAA    ADR1,X
213 A 2121 81B0                 CMPA    #$B0
214 A 2123 7C0006               INC     AR
215 A 2126 22D1                 BHI     DECR1
216 A 2128 7F0007               CLR     ARFLG
217 A 212B 7F0006               CLR     AR
218 A 212E 86FF                 LDAA    #$FF
219 A 2130 970F                 STAA    ARDEL
220 A 2132 39                   RTS
221 A 2133 7C0007       D_RTN   INC     ARFLG
222 A 2136 39                   RTS
223 A
224 A 2137 A633         CONV    LDAA    ADR3,X           ;CONVERSION ROUTINE

225 A 2139 2601                 BNE     C1
226 A 213B 4C                   INCA
227 A 213C 970B         C1      STAA    RATE
228 A 213E A632                 LDAA    ADR2,X
229 A 2140 44                   LSRA
```

Page 4

Appendix I

```
                                        MVAU_002.LST
230 A 2141 44                    LSRA
231 A 2142 44                    LSRA
232 A 2143 44                    LSRA

M68HC11 Absolute Assembler    Version 2.70C:mvau_tx.ASC

233 A 2144 44                    LSRA
234 A 2145 9705                  STAA      INT
235 A 2147 39                    RTS
236 A
237 A 2148 A631        ELAB      LDAA      ADR1,X              ;NOTE CODES
COMPUTING ROUTINE
238 A                  *         LSRA
239 A                  *         LSRA
240 A 214A 5F                    CLRB
241 A 214B CE0003                LDX       #$03
242 A 214E 02                    IDIV
243 A 214F 8F                    XGDX
244 A 2150 CE1000                LDX       #$1000
245 A 2153 970D                  STAA      TEMP
246 A 2155 12088006              BRSET     SW,#$80,E0          ;SCALE 12/M
SELECTION
247 A 2159 BD219D                JSR       SCALA
248 A 215C CE1000                LDX       #$1000
249 A 215F 9102       E0         CMPA      NT1
250 A 2161 2739                  BEQ       E1
251 A 2163 9103                  CMPA      NT2
252 A 2165 2735                  BEQ       E1
253 A 2167 9700                  STAA      NTON
254 A 2169 9605                  LDAA      INT
255 A 216B 270D                  BEQ       EEE
256 A 216D 9600       EE0        LDAA      NTON
257 A 216F 9001                  SUBA      NTOFF
258 A 2171 8130                  CMPA      #$30
259 A 2173 2301                  BLS       EE1
260 A 2175 43                    COMA
261 A 2176 9105       EE1        CMPA      INT
262 A 2178 2F22                  BLE       E1
263 A 217A 9600       EEE        LDAA      NTON
264 A 217C 16                    TAB
265 A 217D BD21BF                JSR       NOTE_ON
266 A 2180 D601                  LDAB      NTOFF
267 A 2182 BD21D3                JSR       NOTE_OFF
268 A 2185 9603                  LDAA      NT2                 ;NOTE QUEUE
UPDATING
269 A 2187 9701                  STAA      NTOFF
270 A 2189 9602                  LDAA      NT1
271 A 218B 9703                  STAA      NT2
272 A 218D 9600                  LDAA      NTON
273 A 218F 9702                  STAA      NT1
274 A 2191 13084007              BRCLR     SW,#$40,E1          ;1/3 NOTE SELECTION

275 A 2195 9600                  LDAA      NTON
276 A 2197 9701                  STAA      NTOFF
277 A 2199 7F0007                CLR       ARFLG
278 A 219C 39          E1        RTS
279 A 219D
280 A 219D 4F          SCALA     CLRA                          ;MAJOR SCALE
COMPUTING ROUTINE
281 A 219E D60D                  LDAB      TEMP                ;ATTN: USES
REGISTERS D, X, Y
282 A 21A0 CE000C                LDX       #$000C
```

```
                                          MVAU_002.LST
283 A 21A3 02                    IDIV
284 A 21A4 18CE2205              LDY       #TABLE
285 A 21A8 183A                  ABY
286 A 21AA 50                    NEGB
287 A 21AB DB0D              *   ADDB      TEMP
288 A 21AD 18EB00                ADDB      $00,Y
289 A 21B0 17                    TBA
290 A 21B1 39                    RTS
0
M68HC11 Absolute Assembler   Version 2.70C:mvau_tx.ASC 291 A
292 A 21B2 A72F        TX        STAA      SCDR,X          ;MIDI TX ROUTINE -
TRANSMITS ACC. A VALUE
293 A 21B4 18CE1000              LDY       #$1000          ;TX DELAY
294 A 21B8 1809        T1        DEY
295 A 21BA 26FC                  BNE       T1
296 A 21BC A62E                  LDAA      SCSR,X          ;SETS THE SERIAL
COMM. DEVICE
297 A 21BE 39                    RTS
298 A
299 A 21BF A62E        NOTE_ON   LDAA      SCSR,X          ;MIDI NOTE ON TX
ROUTINE - TX ACC. B VALUE
300 A 21C1 8690                  LDAA      #$90            ;MIDI CH 0 NOTE ON
CODE
301 A 21C3 BD21B2                JSR       TX
302 A 21C6 17                    TBA
303 A 21C7 8B20                  ADDA      #$20            ;NOTE TO BE PLAYED
EX 28
304 A 21C9 BD21B2                JSR       TX
305 A 21CC A634                  LDAA      ADR4,X
306 A 21CE 44                    LSRA                      ;MIDI VELOCITY CODE 307 A 21CF BD21B2                JSR       TX
308 A 21D2 39                    RTS
309 A
310 A 21D3 A62E        NOTE_OFF  LDAA      SCSR,X          ;MIDI NOTE OFF TX
ROUTINE - TX ACC. B VALUE
311 A 21D5 8690                  LDAA      #$90            ;MIDI CH 0 NOTE ON
CODE
312 A 21D7 BD21B2                JSR       TX
313 A 21DA 17                    TBA
314 A 21DB 8B20                  ADDA      #$20            ;NOTE TO BE STOPPED
EX 28
315 A 21DD BD21B2                JSR       TX
316 A 21E0 4F                    CLRA                      ;SENDS A MIDI
VELOCITY=0 TO STOP THE NOTE
317 A 21E1 BD21B2                JSR       TX
318 A 21E4 39                    RTS
319 A
320 A 21E5 A62E        ANOFF     LDAA      SCSR,X          ;TRASMITS
ALL_NOTES_OFF TO MIDI CH 0
321 A 21E7 86B0                  LDAA      #$B0
322 A 21E9 BD21B2                JSR       TX
323 A 21EC 867B                  LDAA      #$7B
324 A 21EE BD21B2                JSR       TX
325 A 21F1 8600                  LDAA      #$00
326 A 21F3 BD21B2                JSR       TX
327 A 21F6 39                    RTS
328 A
329 A                      ************ SERVICE ROUTINE FOR OUTPUT COMPARE 2
*************
```

Page 6

Appendix I

```
                              MVAU_002.LST
330 A
331 A 21F7 DC09        FTOV      LDD       MSB
332 A 21F9 F31018                ADDD      $1018
333 A 21FC FD1018                STD       $1018
334 A 21FF 8640                  LDAA      #$40
335 A 2201 B71023                STAA      $1023
336 A 2204 3B                    RTI
337 A
338 A                     ************ TABLE ***************
339 A
340 A 2205 0000020204 TABLE      FCB
$00,$00,$02,$02,$04,$05,$05,$07,$07,$09,$09,$0A
           0505070709
           090A
341 A 2211
342 A 2211
343 A                     ************ VECTORS *************
344 A
345 A      FFE6                  ORG       $FFE6
346 A FFE6 21F7                  FDB       FTOV
```
M68HC11 Absolute Assembler   Version 2.70C:mvau_tx.ASC

```
347 A
348 A      FFF8                  ORG       $FFF8
349 A FFF8 2000        BADOP     FDB       INIT
350 A FFFA 2000        COP       FDB       INIT
351 A FFFC 2000        CLOCK     FDB       INIT
352 A FFFE 2000        RESET     FDB       INIT
353 A 0000
354 A                            END
```
SYMBOL TABLE:  Total Entries=  87

| Symbol | Value | Symbol | Value |
|---|---|---|---|
| ADCTL | 0030 | M1 | 2070 |
| ADR1 | 0031 | MAIN | 2047 |
| ADR2 | 0032 | MSB | 0009 |
| ADR3 | 0033 | NOTE_OFF | 21D3 |
| ADR4 | 0034 | NOTE_ON | 21BF |
| ANOFF | 21E5 | NT1 | 0002 |
| AR | 0006 | NT2 | 0003 |
| ARDEL | 000F | NTOFF | 0001 |
| ARFLG | 0007 | NTON | 0000 |
| ARL | 209A | OPTION | 0039 |
| AR_DLY | 2097 | PACTL | 0026 |
| AU1 | 2094 | PORTC | 1003 |
| AU_RG | 207C | PORTD | 0008 |
| BADOP | FFF8 | PORTE | 000A |
| BAUD | 002B | R1 | 204A |
| BIT6 | 0040 | R2 | 2051 |
| BIT7 | 0080 | R3 | 2058 |
| C1 | 213C | R4 | 205F |
| CLOCK | FFFC | RATE | 000B |
| CONV | 2137 | RESET | FFFE |
| COP | FFFA | RG__R | 0020 |
| DDRD | 0009 | R__GR | 0038 |
| DECR1 | 20F9 | R____ | 0018 |
| DECR2 | 2106 | SCALA | 219D |
| DECR3 | 2119 | SCCR1 | 002C |
| DECREM | 20EB | SCCR2 | 002D |
| D_RTN | 2133 | SCDR | 002F |
| E0 | 215F | SCSR | 002E |

```
                             MVAU_002.LST
E1       219C    SPCR            0028
EE0      216D    SW              0008
EE1      2176    T1              21B8
EEE      217A    TABLE           2205
ELAB     2148    TCTL1           0020
FTOV     21F7    TEMP            000D
HDLY     05C0    TFLG1           0023
INCR1    20AD    TMSK1           0022
INCR2    20BA    TOC2            0018
INCR3    20CD    TX              21B2
INCREM   209F    VEL             0004
INIT     2000    _G___           0010
INT      0005    __V__           0008
IPORTC   0003    ___G_           0028
I_RTN    20E7    ____R           0030
LEDS     0000

Total errors: 0
```

Page 8
Appendix I

What is claimed is:

1. A method of using microvariations of a biological living organism to generate a sequence of environmental changes perceptible through one of the human senses, such method comprising the steps of:
   transforming microvariations within a living organism into an analog electrical signal; and
   generating the sequence of environmental changes perceptible through the human senses based on said analog signal.

2. The method of claim 1, wherein the step of generating the sequence of environmental changes further comprises generating music in an environment of said organism.

3. The method of claim 1, wherein the step of generating the sequence of environmental changes further comprises generating a sequence of different lighting conditions in an environment of said organism.

4. The method of claim 3, wherein the step of generating the sequence of different lighting conditions further comprises generating a sequence of different lighting intensities in the environment of said organism.

5. The method of claim 3, wherein the step of generating the sequence of different lighting conditions further comprises generating a sequence of different lighting color spectrums in the environment of said organism.

6. The method of claim 1, wherein the step of generating the sequence of environmental changes further comprises generating a sequence of different moisture levels in an environment of said organism.

7. The method of claim 1, wherein the step of generating the sequence of environmental changes further comprises generating a sequence of air movement conditions in an environment of said organism.

8. The method of claim 7, wherein the step of generating the sequence of air movement conditions further comprises controlling a fan speed.

9. The method of claim 7, wherein the step of generating the sequence of air movement conditions further comprises controlling the orientation of a fan.

10. The method of claim 1, wherein the step of generating the sequence of environmental changes further comprises generating a sequence of different aroma conditions in an environment of said organism.

11. The method of claim 10, wherein the step of generating the sequence of different aroma conditions in the environment of said organism further comprises evaporating a sequence of different aroma chemicals into the air in the environment of said organism.

12. The method of claim 10, wherein the step of generating the sequence of different aroma conditions further comprises Varying over time the evaporation rate of an aroma chemical in the environment of said organism.

13. The method of claim 1, where the step of generating the sequence of environmental changes based on said analog signal comprises:
   periodically converting said analog signal to a digital signal using an analog to digital converter;
   utilizing said periodically converted digital signal as an input to a sequence generating program running on a microprocessor; and
   outputting digital environmental control data from said microprocessor.

14. The method of claim 13, wherein the step of generating the sequence of environmental changes further comprises generating music in the environment of said organism.

15. The method of claim 14, wherein said digital environmental control codes comprise MIDI synthesizer control codes.

16. The method of claim 15, further comprising the step of controlling a MIDI music synthesizer with said MIDI synthesizer control codes.

17. The method of claim 14 wherein said digital environmental control codes comprise compact disc player control codes, and further comprising the step of controlling the sequence of musical tracks played on a compact disc player using said compact disc player control codes.

18. The method of claim 14 wherein said digital environmental control codes comprise music volume control codes, and further comprising controlling the volume of a music source through said music volume control codes.

19. The method of claim 13, wherein the step of generating a sequence of environmental changes further comprises generating a sequence of air movement conditions in an environment of said organism.

20. The method of claim 19, wherein the step of generating a sequence of air movement conditions in the environment of said organism comprises controlling a fan speed.

21. The method of claim 19, wherein the step of generating a sequence of air movement conditions in the environment of said organism comprises controlling the orientation of a fan.

22. The method of claim 13, wherein the step of generating a sequence of environmental changes further comprises generating a sequence of different moisture levels in an environment of said organism.

23. The method of claim 13, wherein the step of generating a sequence of environmental changes further comprises generating a sequence of different aroma conditions in an environment of said organism.

24. The method of claim 23, wherein the step of generating a sequence of different aroma conditions further comprises evaporating a sequence of different aroma chemicals into the air in an environment of said organism.

25. The method of claim 24, wherein the step of generating a sequence of different aroma conditions in the environment of said organism comprises varying over time the evaporation rate of an aroma chemical in the environment of said organism.

26. The method of claim 13, wherein the step of generating a sequence of environmental changes further comprises generating a sequence of different lighting conditions in an environment of said organism.

27. The method of claim 26, wherein the step of generating a sequence of different lighting conditions in the environment of said organism comprises generating a sequence of different lighting intensities in the environment of said organism.

28. The method of claim 13, wherein the step of generating a sequence of different lighting conditions further comprises generating a sequence of different lighting color spectrums in the environment of said organism.

29. The method of claim 13, further comprising:
   providing a digital feedback signal from said microprocessor;
   applying said digital feedback signal to a DAC to produce an analog feedback signal;
   using said analog feedback signal to level-shift the range of the analog signal applied to said analog to digital converter; and
   periodically updating said digital feedback signal to keep said analog signal in-range for said analog to digital converter.

30. An apparatus that uses microvariations of a biological living organism to generate a sequence of environmental changes perceptible through one of the human senses, such apparatus comprising:
   means for transforming microvariations within a living organism into an analog electrical signal; and
   means for generating a sequence of changes perceptible through the human senses based on said analog signal.

31. The apparatus of claim 30, wherein the means for generating the sequence of environmental changes further comprises means for generating music in an environment of said organism.

32. The apparatus of claim 30, wherein the means for generating the sequence of environmental changes further comprises means for generating a sequence of different lighting conditions in the environment of said organism.

33. The apparatus of claim 32, wherein the means for generating the sequence of different lighting conditions further comprises means for generating a sequence of different lighting intensities in the environment of said organism.

34. The apparatus of claim 32, wherein the means for generating the sequence of different lighting conditions further comprises means for generating a sequence of different lighting color spectrums in the environment of said organism.

35. The apparatus of claim 30, wherein the means for generating the sequence of environmental changes further comprises means for generating a sequence of different moisture levels in the environment of said organism.

36. The apparatus of claim 30, wherein the means for generating the sequence of environmental changes further comprises means for generating a sequence of air movement conditions in the environment of said organism.

37. The apparatus of claim 36, wherein the means for generating the sequence of air movement conditions further comprises means for controlling a fan speed.

38. The apparatus of claim 36, wherein the means for generating the sequence of air movement conditions further comprises means for controlling the orientation of a fan.

39. The apparatus of claim 30, wherein the means for generating the sequence of environmental changes further comprises means for generating a sequence of different aroma conditions in the environment of said organism.

40. The apparatus of claim 39, wherein the means for generating the sequence of different aroma conditions in the environment of said organism further comprises means for evaporating a sequence of different aroma chemicals into the air in the environment of said organism.

41. The apparatus of claim 39, wherein the means for generating the sequence of different aroma conditions further comprises means for varying over time the evaporation rate of an aroma chemical in the environment of said organism.

42. The apparatus of claim 30, where the means for generating the sequence of environmental changes based on said analog signal comprises:
means for periodically converting said analog signal to a digital signal using an analog to digital converter;
means for utilizing said periodically converted digital signal as an input to a sequence generating program running on a microprocessor; and
means for outputting digital environmental control data from said microprocessor.

43. The apparatus of claim 42, wherein the means for generating the sequence of environmental changes further comprises means for generating music in the environment of said organism.

44. The apparatus of claim 43, wherein said digital environmental control codes comprise MIDI synthesizer control codes.

45. The apparatus of claim 44, further comprising the controlling a MIDI music synthesizer with said MIDI synthesizer control codes.

46. The apparatus of claim 43 wherein said digital environmental control codes comprise compact disc player control codes, and further comprising the means for controlling the sequence of musical tracks played on a compact disc player using said compact disc player control codes.

47. The apparatus of claim 43 wherein said digital environmental control codes comprise music volume control codes, and further comprising means for controlling the volume of a music source through said music volume control codes.

48. The apparatus of claim 42, wherein the step of generating a sequence of environmental changes further comprises means for generating a sequence of air movement conditions in an environment of said organism.

49. The apparatus of claim 48, wherein the means for generating a sequence of air movement conditions in the environment of said organism comprises means for controlling a fan speed.

50. The apparatus of claim 48, wherein the means for generating a sequence of air movement conditions in the environment of said organism comprises means for controlling the orientation of a fan.

51. The apparatus of claim 42, wherein the step of generating a sequence of environmental changes further comprises means for generating a sequence of different moisture levels in an environment of said organism.

52. The apparatus of claim 42, wherein the means for generating a sequence of environmental changes further comprises means for generating a sequence of different aroma conditions in an environment of said organism.

53. The apparatus of claim 52, wherein the means for generating a sequence of different aroma conditions further comprises means for evaporating a sequence of different aroma chemicals into the air in an environment of said organism.

54. The apparatus of claim 53, wherein the means for generating a sequence of different aroma conditions in the environment of said organism comprises means for varying over time the evaporation rate of an aroma chemical in the environment of said organism.

55. The apparatus of claim 42, wherein the means for generating a sequence of environmental changes further comprises means for generating a sequence of different lighting conditions in an environment of said organism.

56. The apparatus of claim 55, wherein the means for generating a sequence of different lighting conditions in the environment of said organism comprises means for generating a sequence of different lighting intensities in the environment of said organism.

57. The apparatus of claim 42, wherein the means for generating a sequence of different lighting conditions further comprises means for generating a sequence of different lighting color spectrums in the environment of said organism.

58. The apparatus of claim 42, further comprising:
means for providing a digital feedback signal from said microprocessor;
means for applying said digital feedback signal to a DAC to produce an analog feedback signal;
means for using said analog feedback signal to level-shift the range of the analog signal applied to said analog to digital converter; and
means for periodically updating said digital feedback signal to keep said analog signal in-range for said analog to digital converter.

59. An apparatus that uses microvariations of a biological living organism to generate a sequence of environmental changes perceptible through one of the human senses, such apparatus comprising:
signal conditioning electronics adapted to transform microvariations within a living organism into an analog electrical signal; and
an environment enhancing processor adapted to generate the sequence of environmental changes perceptible through the human senses based on said analog signal.

* * * * *